US007111625B2

(12) United States Patent
Jackson

(10) Patent No.: US 7,111,625 B2
(45) Date of Patent: Sep. 26, 2006

(54) DEMAND VALVES FOR BREATHING APPARATUS

(75) Inventor: Peter J. Jackson, Findon (GB)

(73) Assignee: International Safety Instruments, Inc., Lawrenceville, GA (US)

(*) Notice: Subject to any disclaimer, the term of this patent is extended or adjusted under 35 U.S.C. 154(b) by 6 days.

(21) Appl. No.: 10/859,013

(22) Filed: Jun. 2, 2004

(65) Prior Publication Data

US 2004/0244797 A1 Dec. 9, 2004

(30) Foreign Application Priority Data

Jun. 6, 2003 (GB) ................................ 0313080.4

(51) Int. Cl.
*A62B 9/02* (2006.01)
*A62B 18/10* (2006.01)
*B63C 11/02* (2006.01)
*A61M 16/00* (2006.01)

(52) U.S. Cl. .......................... 128/205.24; 128/201.27; 128/201.28; 128/204.26; 128/207.12

(58) Field of Classification Search ........... 128/204.26, 128/205.24, 204.24, 201.22, 201.27, 201.28, 128/201.29, 206.15, 206.21, 207.12; 251/114, 251/90; 137/908
See application file for complete search history.

(56) References Cited

U.S. PATENT DOCUMENTS 2,970,602 A * 2/1961 Cupp .................... 137/505.43
3,123,976 A * 3/1964 Mansell ........................ 60/327
3,134,520 A * 5/1964 Wentz ........................ 222/399
3,145,689 A * 8/1964 O'Neal ..................... 116/34 R
3,411,533 A * 11/1968 Puster ........................ 137/557
3,795,257 A * 3/1974 Fabish et al. ............... 137/491
4,134,421 A * 1/1979 Cameron .................... 137/316
5,357,950 A 10/1994 Wippler et al.
6,000,473 A * 12/1999 Reilly ......................... 169/17
6,016,802 A * 1/2000 Jackson ................ 128/205.25
6,029,749 A * 2/2000 Reilly et al. .................. 169/17
6,336,667 B1 * 1/2002 Ford et al. .................... 292/25
6,966,316 B1 * 11/2005 Lowry .................. 128/204.26

* cited by examiner

*Primary Examiner*—Henry Bennett
*Assistant Examiner*—Annette Dixon
(74) *Attorney, Agent, or Firm*—Rodgers & Rodgers

(57) ABSTRACT

There is described a demand valve for a breathing apparatus with a "first breath" mechanism, wherein a demand valve is held closed by resiliently latching an operating diaphragm of the valve in a position wherein the valve is closed. The diaphragm is resiliently biased towards opening the valve, and the resilient latch is arranged to exert sufficient force so as not to be overcome by the resilient bias alone, but so as to be overcome by the combination of the resilient bias and a predetermined pressure difference across the diaphragm caused by sub-ambient pressure within the facepiece of the breathing apparatus.

18 Claims, 8 Drawing Sheets

PRIOR ART

PRIOR ART

PRIOR ART

PRIOR ART

DEMAND VALVES FOR BREATHING APPARATUS

BACKGROUND OF THE INVENTION

This invention relates to demand valves for breathing apparatus, whereby breathable gas, stored under pressure, is supplied to a face-piece, hood or helmet at a rate according to the respiratory requirements of the wearer, whilst at the same time maintaining a super-ambient, or positive, pressure within the face-piece, hood or helmet so as to prevent any inward leakage of ambient atmosphere.

Positive pressure demand valves for breathing apparatus are well known and employ a variety of mechanisms to control the flow of gas to the wearer according to his requirements, such mechanisms being actuated by movement of a pressure responsive diaphragm having an outer face exposed to ambient pressure and an inner face exposed to pressure within the face-piece such that, when the wearer inhales, causing a drop in pressure within the face-piece, the diaphragm moves inwards, actuating the valve mechanism to admit gas to the face-piece at a rate proportional to the pressure drop. When inhalation ceases, equilibrium is restored and the valve closes. In order to maintain a small positive pressure within the face-piece, the valve is biased open, typically by means of a spring bearing against the outer face of the diaphragm such that a superambient pressure of, say, 2 millibar within the face-piece is required to move the diaphragm outwards against the spring and thus close the valve. The wearer's exhaled breath is vented from the face-piece to the surrounding atmosphere through a simple non-return valve which is biased closed with a spring so as to only open when pressure within the face-piece exceeds ambient pressure by, say, 4 millibar. Thus it may be seen that pressure within the face-piece is continuously maintained at a level of between, say, 2 and 4 millibar above that of the surrounding atmosphere and, by this means, any leakage due to damage or imperfect sealing of the face-piece can only be outwards, so preventing any ingress of ambient atmosphere to the face-piece.

It may be seen that, with this arrangement, the demand valve cannot close unless the face-piece is effectively sealed and thus some means must be provided whereby the supply of gas to the face-piece may be interrupted when the face-piece is not being worn, in order to prevent significant loss of breathing gas through the demand valve. In some cases, the supply of gas to the demand valve may simply be isolated by closing a suitable valve provided for that purpose. However, there are circumstances when this expedient is not practicable or is inconvenient to the wearer and, for this reason, the demand valve may incorporate what is commonly referred to as a "first-breath" device.

The "first-breath" device is a mechanism which may be manually set to hold the demand valve in a closed state so that no gas may pass through it until such time that a significant sub-ambient pressure is sensed within the face-piece by the pressure responsive diaphragm of the demand valve, whereupon inward force applied by the diaphragm overcomes, or releases, the mechanism and restores the demand valve to its normal positive pressure operation. Sub-ambient pressure within the face-piece would normally only result from inhalation by the wearer with the face-piece effectively sealed. Thus the initial inhalation (or "first breath") taken by the wearer, trips the mechanism and releases the demand valve from the "closed" state, returning it to normal positive pressure operation.

In readiness for using the breathing apparatus, the wearer manually sets the first-breath mechanism to close the demand valve, and connects the gas supply thereto. The wearer may then either keep the face-piece to hand, ready for donning, or may don the face-piece with the demand valve disconnected from it and breathe ambient air through the demand valve connection port until the demand valve is re-connected, or may breathe ambient air through a separate manually opened breathing port in the face-piece, in all cases without any loss of breathing gas. As soon as the face-piece is sealed, either by attaching the demand valve or by closing the breathing port, the wearer's first inhalation will operate the first-breath mechanism and thereafter the demand valve will supply breathing gas to the wearer according to his requirements, at the same time maintaining a positive or superambient pressure within the face-piece.

The present invention provides a simple and reliable First-Breath mechanism for breathing apparatus demand valves.

One aspect of the invention provides a demand valve operated by a diaphragm movable between a first position in which the valve is closed and a second position in which the valve is open to supply gas to a user, the diaphragm being retainable in the first position by a resilient latch which is releaseable by a force produced by a predetermined pressure differential across the diaphragm.

The demand valve includes setting means for moving the diaphragm to the first position, preferably in the form of a setting lever pivoted to the housing of the valve and engageable with the diaphragm. The resilient latch may operate between the setting lever and the housing, and may comprise a detent fixed on the housing and a resilient element mounted to or forming part of the setting lever.

One embodiment of this aspect of the invention provides a demand valve for a breathing apparatus having a pilot valve operated by a pivoting pilot lever, and a first-breath mechanism comprising a resilient latch operable to hold the pilot valve closed against its normal opening bias, but arranged to release the pilot lever when sub-ambient pressure is present in the facepiece of the breathing apparatus.

A further aspect of the invention provides a breathing apparatus incorporating such a demand valve.

An example of a demand valve incorporating the first-breath arrangement of the invention will now be described with reference to the accompanying drawings, in which.

Figure 1:
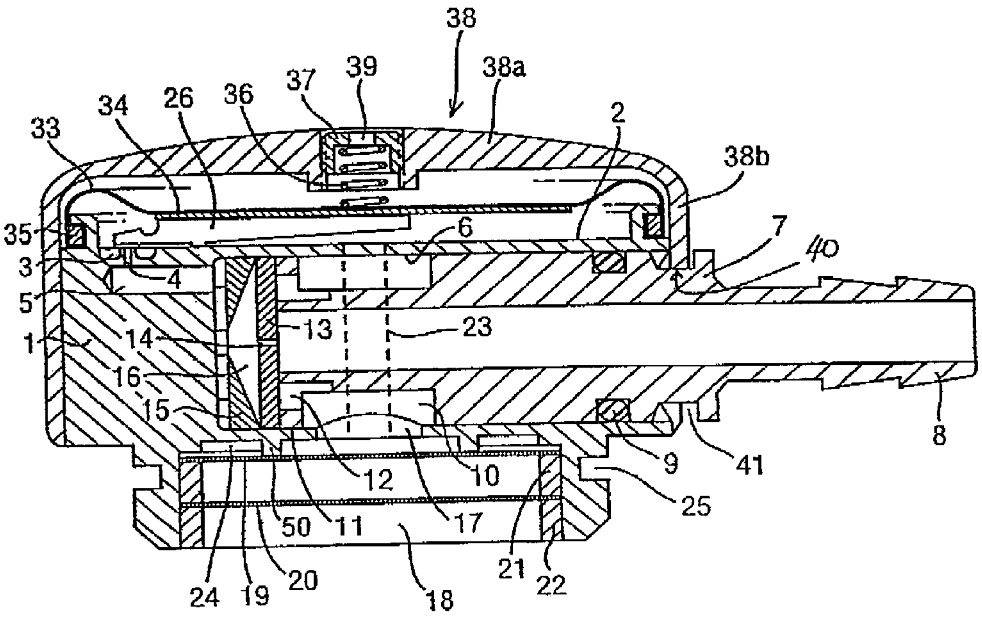
FIG. 1 shows a sectional elevation of a conventional demand valve in its closed condition.

Referring now to FIG. 1, the demand valve comprises a cylindrical body 1 having a flat end face 2 into which is formed an annular recess 3. At the center of the recess 3 projects a substantially cylindrical nozzle or jet 4, the end face of which is level with end face 2. A bore 5 links the jet 4 with a radially-extending inlet bore 6.

Received in the inlet bore 6 is a tubular inlet stem 7 which is free to rotate within the inlet bore and which has as its outer end formed a barbed stem 8 for connection to a supply hose. Alternative connection means for connecting a supply hose may be used instead of the barbed stem 8, such as a threaded or bayonet connection. An annular seal 9 is housed in a groove extending around the inlet stem 7. Close to the inner end of the stem, the stem has a portion of reduced diameter so as to form an annular chamber 10 between the stem and the inlet bore 6 and to define a flange 11 at the inner end of the stem. The flange 11 is formed with a number of openings 12 providing communication between the chamber 10 and the circular face of the flange.

Figure 2:
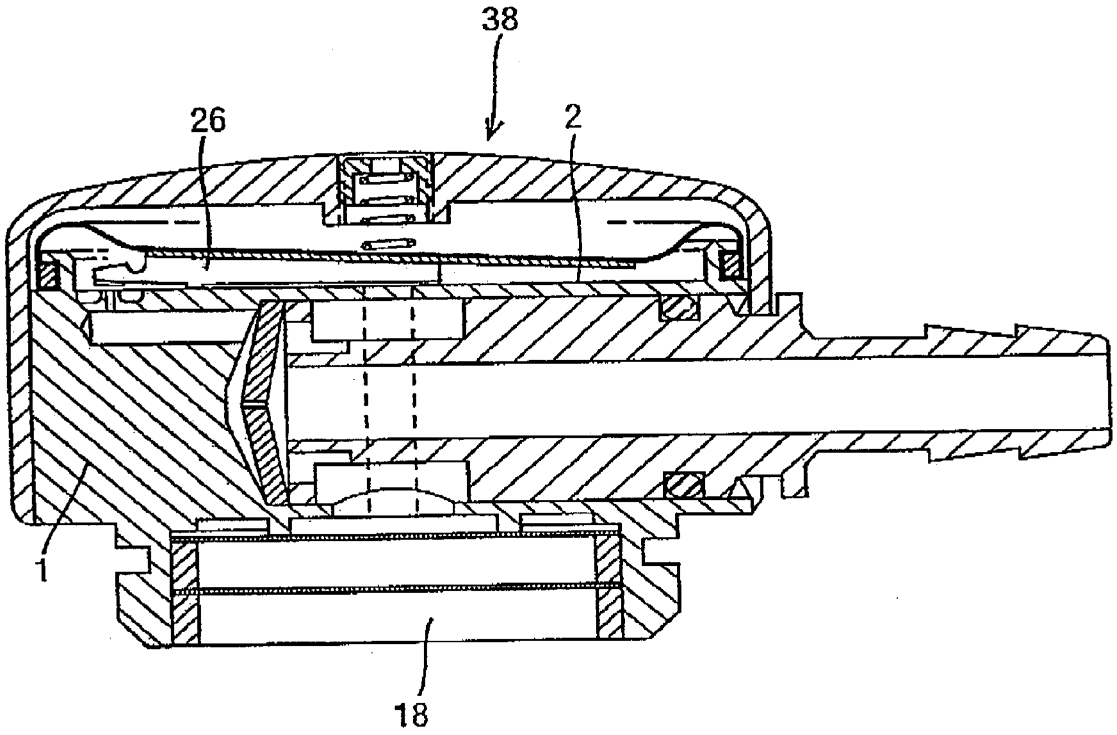
FIG. 2 shows a sectional elevation of the valve of FIG. 1 in its open condition.
Figure 3:
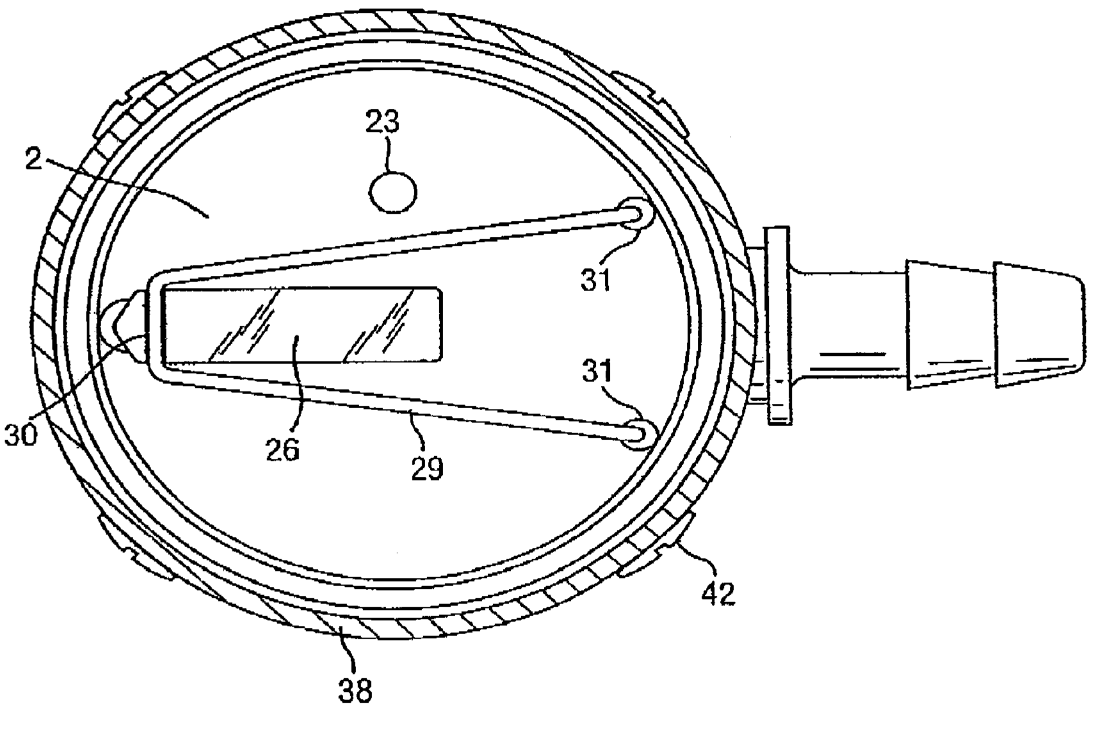
FIG. 3 shows a plan view of the valve showing the pilot lever of the valve of FIGS. 1 and 2 and its retaining wire form.
Figure 4A:
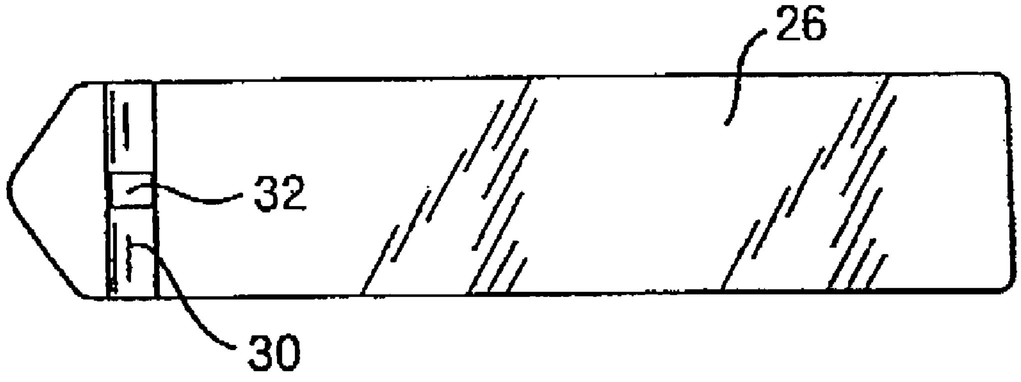
FIG. 4 shows three views of the pilot lever.
Figure 4B:
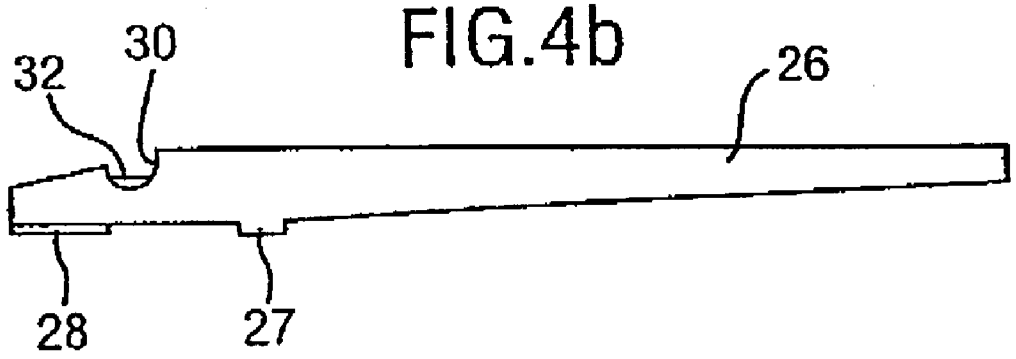
PRIOR ART FIG.4b
Figure 4C:
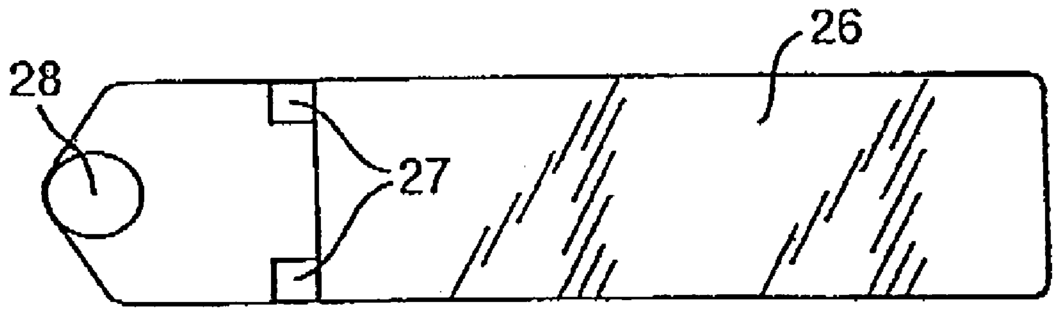
PRIOR ART FIG.4c

Adjacent to the face of the flange there is a resilient valve disc 13, the periphery of which seals against the wall of the inlet bore 6 in the body. The centre of the valve disc is penetrated by a metering orifice 14. Between the valve disc and the end face of the inlet bore, there is positioned a dished supporting disc 15 which, with the valve disc 13, forms a conical or domed chamber 16, this chamber 16 being in communication with the bore 5 and the jet 4, by means of channels in the supporting disc. Alternatively, the end of the lateral bore itself may be made concave so as to form the chamber 16, as is shown in FIG. 2.

A port 17 in the body communicates between the annular chamber 10 and an outlet bore 18 which houses a pair of wire screens 19 and 20, which are spaced apart and secured within the outlet bore 18 by means of tight fitting rings 21 and 22. A port 23 through the body communicates between the area 24 behind the first screen 19 and end face 2. The valve body 1 is adapted, by means of a groove 25 or by other suitable attachment means, such as a screw thread or bayonet fitting, to connect in a leak tight manner to a corresponding attachment means on the face-piece.

A pilot lever 26 has two projections 27 which engage end face 2 and a third projection 28 which is in contact with the face of jet 4, the lever being held in this position by means of a spring wire form 29 located in a groove 30 in the lever and having its ends secured in holes 31 in the body. A ridge 32 across the groove in the lever, upon which the wire form bears, ensures that the force applied by the wire form is substantially evenly applied to the projections upon which the lever stands, even if that part of the wire form which passes through the groove is not parallel to surface 2. The lever is so shaped that it can be tilted to a limited degree about the axis defined by the two projections 27 in contact with face 2 such that, when so tilted, the third projection 28 is moved away from the jet 4. Situated above the lever is a flexible diaphragm 33 having a rigid central plate 34 and a flexible sealing bead 35 around its periphery so shaped as to fit into and seal in a groove formed in a rim surrounding end face 2.

The diaphragm 33 is urged into contact with the pilot lever 26 by means of a biasing spring 36, having one end in contact with the diaphragm and the other end retained in a recess in an adjusting screw 37 threaded into a central boss in a rigid cover 38. The end of the pilot lever 26 remote from the jet 4 is positioned centrally of the diaphragm 33, so that downward movement of the diaphragm (as seen in FIGS. 1 and 2) will rock the pilot lever to open the jet 4. A vent hole 39 in the adjusting screw, or elsewhere in the cover, admits ambient pressure to the region above the diaphragm. The cover 38 has an arched cut-out 40 which engages with a groove or step 41 around the inlet stem 7 so as to retain the inlet stem in the lateral bore of the body and allow the stem to rotate. The cover 38 is secured to the body 1 by screws 42 or by other appropriate securing means.

In operation of the demand valve breathable gas under pressure enters the valve from a supply hose, passes through the tubular inlet stem 7, urging the resilient valve disc 13 away from the flange 11 of the inlet stem, allowing gas to pass through the openings 12 in flange 11 to the annular chamber 10 and thence to port 17 and the outlet bore 18 and finally to the face-piece. At the same time, a small continuous flow of gas passes through the metering orifice 14 in the valve disc 13 into the domed chamber 16 behind the disc, from whence it can escape through the axial hole 5 in jet 4, the lever 26 being held in a tilted position by the biasing spring 36 bearing against the diaphragm, such that the projection 28 on the lever is held away from the jet 4. The small flow of gas from the jet escapes freely from the area under the diaphragm through port 23 to the outlet bore 18.

Flow of gas from the outlet bore 18 causes pressure to rise within the face-piece, since the escape of air from the facepiece is controlled by a spring loaded exhalation valve. The pressure increase is communicated via port 23 to the area under the diaphragm 33 where it urges the diaphragm upward (as seen in the Figures) against the biasing spring 36. This movement of the diaphragm releases pressure on the end of the pilot lever 26 remote from the jet 4, allowing the pilot lever to rotate under the influence of the spring wire form 29 to bring projection 28 closer to, the jet 4. As the projection 28 approaches the jet 4, the flow of gas from the chamber 16 is progressively restricted until the outflow of gas is less than the flow through the metering orifice 14, and pressure in the chamber 16 rises due to the continuous inflow of gas to the chamber through the metering orifice 14 in the resilient valve disc 13. The increased pressure in the chamber 16 urges the resilient valve disc 13 back against the flange 11 on the inlet stem, thus obstructing the openings 12 in the flange and preventing further flow of gas to the outlet bore 18.

Any subsequent reduction in pressure within the face-piece will cause the diaphragm 33 to move inwards under the influence of the biasing spring 36, thus tilting the pilot lever to once again open the jet 4, allowing pressure within the chamber 16 to fall such that the valve disc 13 will be urged away from the face of flange 11 by the pressure of the incoming gas, allowing a flow of gas through the openings 12 to the outlet and hence to the face-piece. The outlet screens 19 and 20 serve to diffuse the flow of gas out of the valve and also to provide the desired degree of pressure feedback via port 23 to the area under the diaphragm.

A preferred embodiment of a First-Breath mechanism according to the present invention is seen in FIGS. 5 to 8, and comprises of a modified demand valve cover 38 in which is fixed a cylindrical post 43 projecting towards the upper face of the diaphragm 34. The post 43 has a shank **43*a* which terminates in a head 43*b* of a larger diameter than the shank 43*a*, the head having oppositely-facing conical surfaces. Divergent detent surfaces 43*c* face away from the diaphragm 34, while convergent cam surfaces 43*d* face towards the diaphragm 34**.

A resilient arm 44 formed from spring wire has two parallel legs joined at one of their respective ends by a cross bar 45, and is retained in the cover 38 by a retaining member 46, such that the arm 44 is free to rotate about the axis of the cross bar 45, but is restrained from movement in any other direction. Each leg of the resilient arm 44 is generally “L” shaped, having a short portion **44*a* adjacent the crossbar 45 and a longer portion 44*b* at a right angle to the short position 44*a***.

A resilient button 47 is mounted to the cover 38 and has a rigid insert 48, formed with a flat end face 48*a*. The insert 48 is movable radially inwardly of the valve by depressing the button 47, and release of the button 47 allows it to spring back to its original position, retracting the insert 48. When the button 47 is depressed, the end face 48*a* of the insert bears against the shorter portions 44*a* of the legs of the resilient arm 44 rotating the arm 44 about the axis of the cross bar 45 and forcing the longer portions 44*b* of the legs of the resilient arm 44 over the conical head 43*b* of the post 43. When released, the resilient button returns to its original position, clear of the arm 44. The gap between the leg portions 44*a* of the resilient arm 44 is approximately the same as the diameter of the shank 43*a* of the post 43 so that the leg portions 44*b* must spread apart as they are forced over the conical cam surfaces 43*d* of the head of the post and will then spring back again as they pass over the conical detent surface 43*c* of the head to lightly grip the shank 43*a* of the post.

Figure 5:
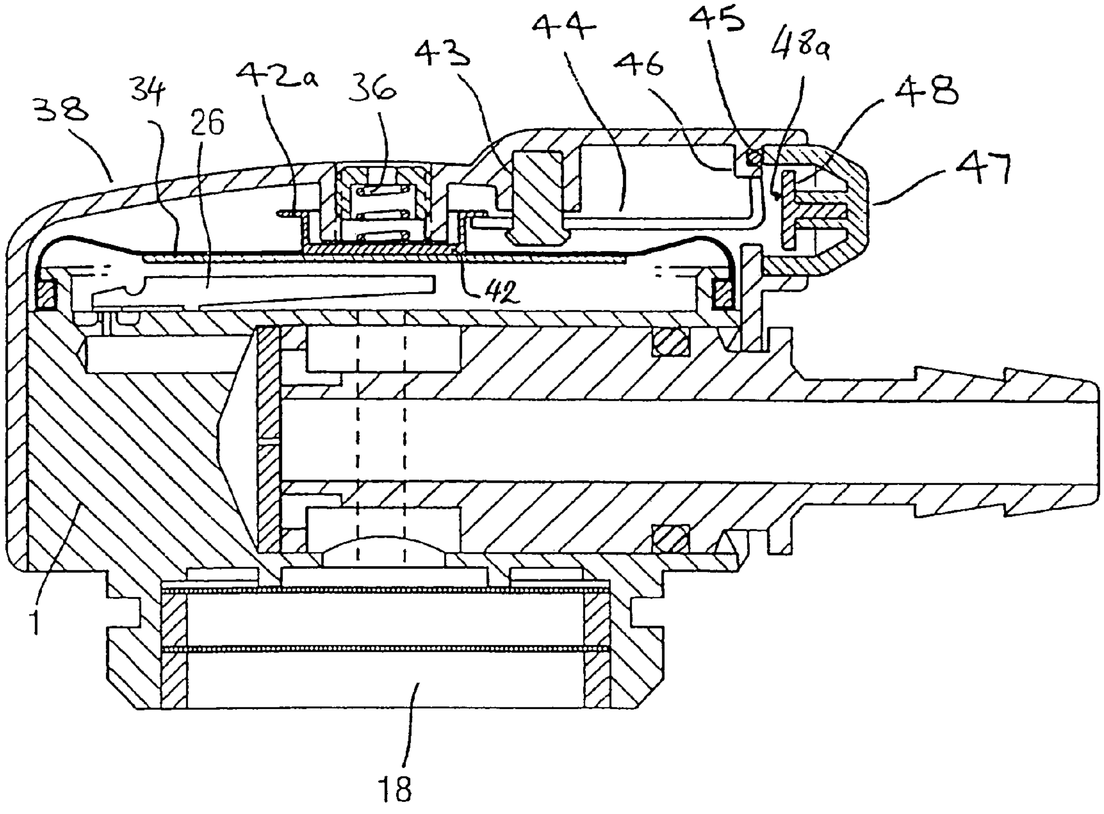
FIG. 5 shows a sectional elevation of a valve similar to that of FIG. 1 and incorporating a first-breath mechanism of the invention, in its closed condition.

The free ends of the leg portions 44*b* of the resilient arm 44 lie between the upper face of the central part 34 of the diaphragm 33 and the underside of a flange 42*a* formed on a circular cup 42 which is fixed to the central part 34 of the diaphragm 33 such that, as the leg portions 44*b* of the arm 44 are forced over the head of the post 43 by depressing the button 47, as previously described, the ends of the leg portions 44*b* engage the underside of flange 42*a* and lift the diaphragm 33 clear of the pilot lever 26, as shown in FIG. 5. The diaphragm 33 will remain held in this position until sufficient force is applied to pull the leg portions 44*b* of the spring clip back over the conical detent surface 43*c* of the head 43*b* of the post 43. The force required to release the arm 44 is arranged to be substantially greater than the force applied by the positive pressure biasing spring 36 by selecting the diameter and material 5 of the wire forming the resilient arm 44. With the diaphragm thus held in this position, the pilot lever 26 closes the jet 4 and the valve disc 13 closes the openings 12 so that no gas will flow to the outlet bore 18.

In FIG. 5 the diaphragm 34 is shown parallel to the face 2 of the body of the demand valve. It will be appreciated that due to the spring 36 pressing centrally in the cup 42, and the arm 44 engaging the peripheral flange 42*a* of the cup, the diaphragm may tilt and contact the pilot lever 26. In the arrangement of FIG. 5, the edge of the rigid part 34 of the diaphragm will contact the pilot lever 26 at a point between the projections 27 and the projection 28, and will thus not cause projection 28 to lift away from jet 4. It will be appreciated that contact between the diaphragm 33 and that part of the pilot lever to the right (in the Figure) of the projections 27 should be avoided if the diaphragm is tilted when the arm 44 engages the post 43.

Figure 6:
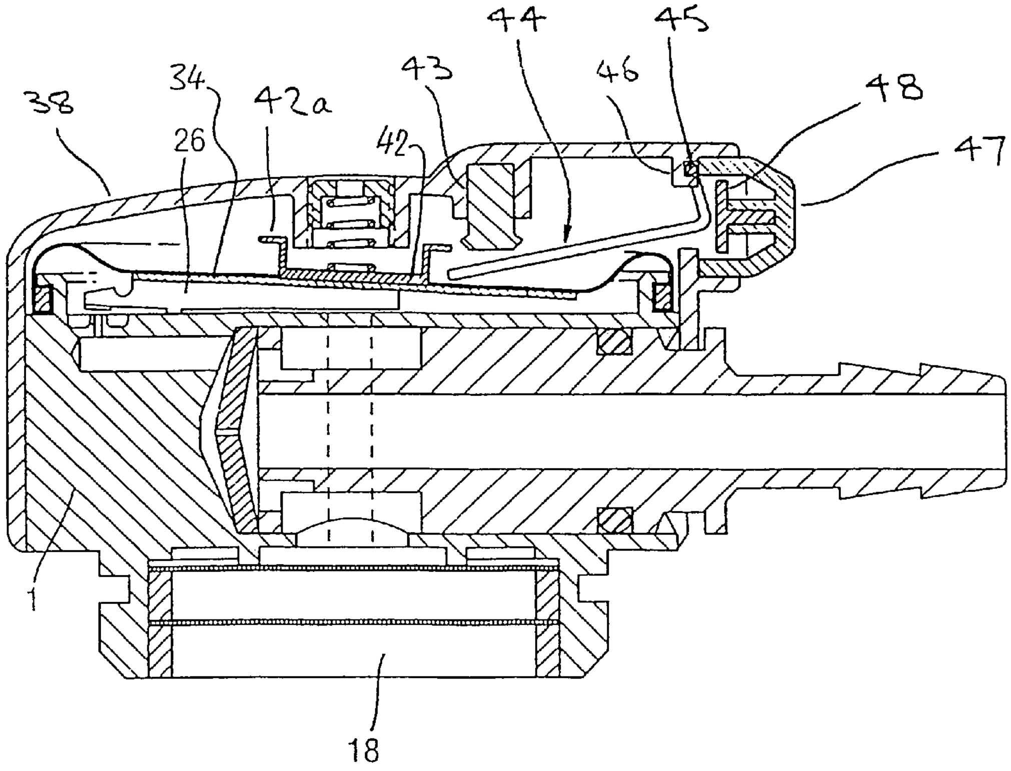
FIG. 6 shows a sectional elevation of the valve of FIG. 5 in its open condition.
Figure 7:
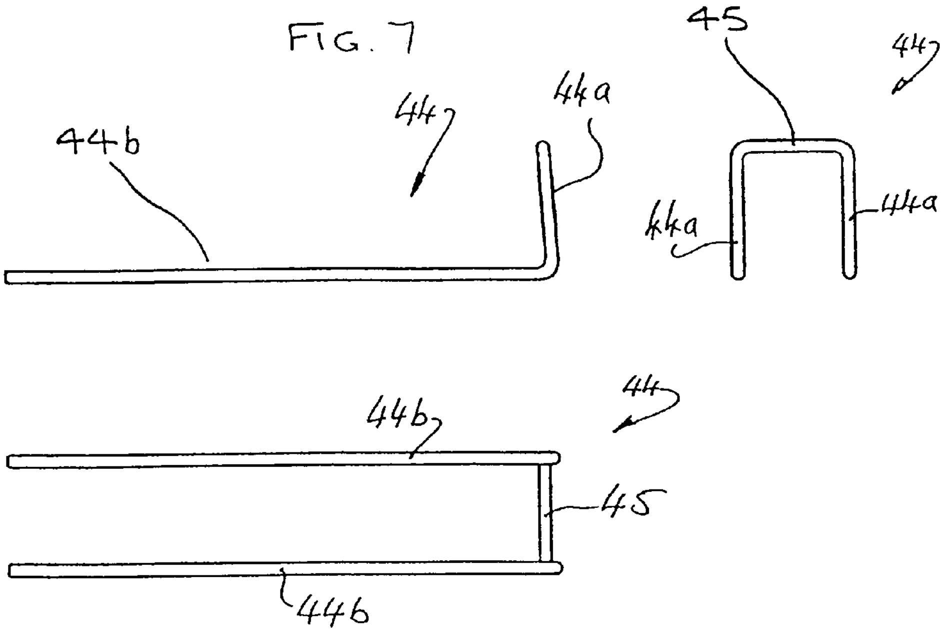
FIG. 7 shows three views of the resilient arm.
Figure 8:
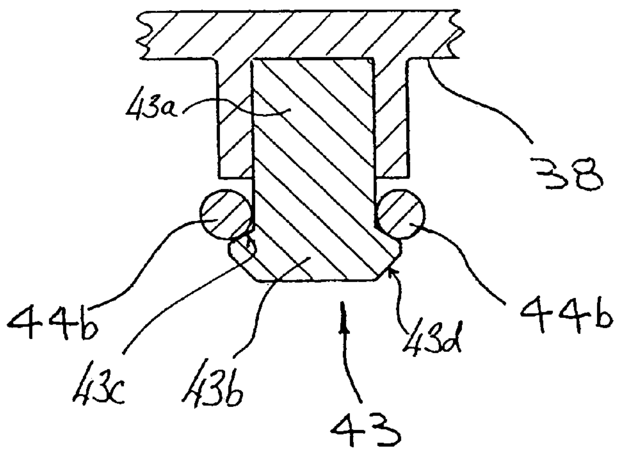
FIG. 8 shows the resilient arm engaged on the second detent.

When the face-piece is sealed, the wearer's initial inhalation will create a substantial drop in pressure within the face-piece, drawing the diaphragm 33 inwards with sufficient force to pull the leg portions 44*b* of the arm 44 over the detent surfaces 43*c* of the head 43*b* of the post 43, thus allowing the diaphragm to again make contact with the pilot lever 26 and open the valve to admit gas to the face-piece, as shown in FIG. 6. In this position, the arm 44 is free to rotate about the axis of the cross bar 45 and thus does not interfere with subsequent movement of the diaphragm. The mass of the arm is small and so has no significant effect upon the operation of the demand valve.

Figure 9:
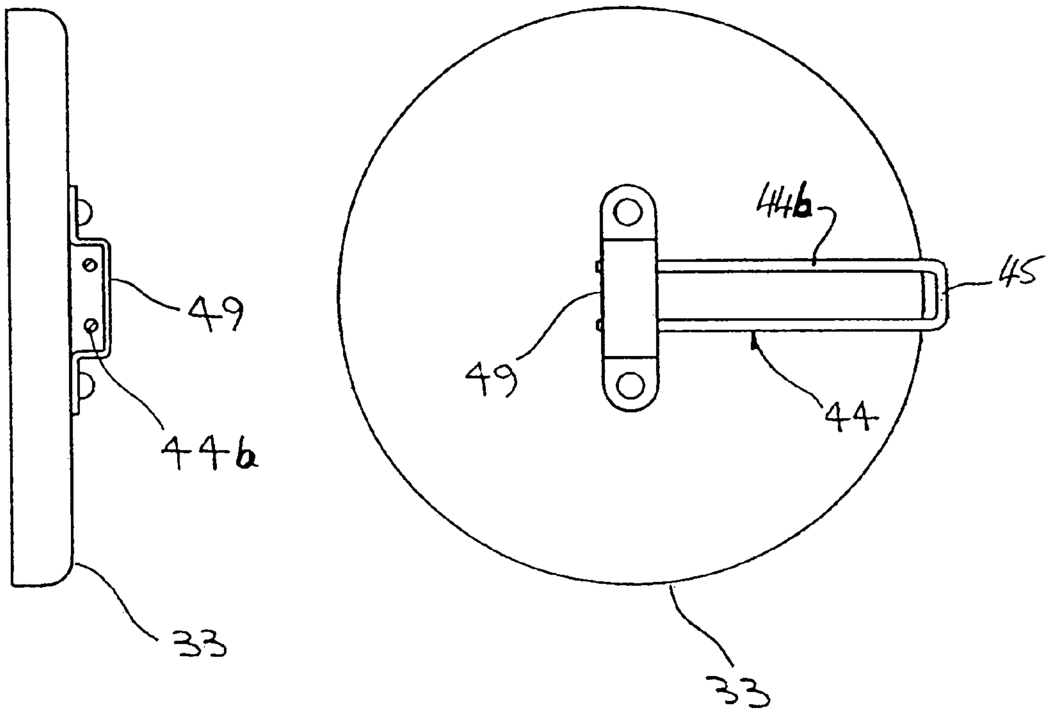
FIG. 9 shows a saddle fixed to the diaphragm.

It will be understood that a First-Breath mechanism according to the present invention may vary somewhat in the details of its construction from the preferred embodiment here described. For example, the flanged cup 42 nay be replaced by a bracket or saddle 49 as shown in FIG. 9. Also, the post 43 may be rectangular in cross-section rather than cylindrical as described. The means provided to manually rotate the arm 44 and so lift the diaphragm, may take the form of a lever or a spring loaded plunger or other device, rather than a resilient button as shown, and may be operated by rotating, pressing or pulling. It is also foreseen that detent surfaces 43*c* of the post 43 may be replaced by a pair of detent surfaces which engage the leg portions 44*b* to resiliently compress them together rather than spread them as the arm 44 engages the detent. Moreover, the arm 44 may comprise a single resilient portion 44*b* which engages the post 43 on one side only, the arm 44 being deflected resiliently as it passes over cam surface 43*d* and detent 43*c*.

Furthermore, the resilient latching between the arm 44 and the cover 38 may be achieved by a resilient latching element fixedly mounted to the cover which engages a rigid swinging arm 44.

In a yet further alternative embodiment, the resilient button 47 may be replaced by a latching element which is operable to latch the insert 48 in its position engaging the arm 44. In such an arrangement, the arm 44 will engage a detent on the diaphragm to hold the diaphragm away from the pilot lever, and the insert 48 will be held in its "pushed in" position by a resilient latch which is overcome by the wearer's first breath.

In a further development, a manual release arrangement may be included to disengage the arm 44 from the detent post 43. Such an arrangement may include, for example, a movable pushrod extending through the rigid cover 38 and engageable with the arm 44 or with the diaphragm to move the arm or diaphragm downwards as seen in FIG. 5 to disengage the arm 44 from the post 43. Such an arrangement could also function as a selectively-operable override to the pilot operation of the valve seen in FIG. 5, by moving the diaphragm sufficiently to open the jet 4. The manual release may be used if a malfunction of the engagement between the arm 44 and the post 43 prevents the wearer's inhalation from lowering the pressure within the facemask sufficiently for the pressure difference across the diaphragm alone to release the latch, or if the vent 39 becomes obstructed and ambient pressure no longer acts on the outer face of the diaphragm.

The invention claimed is:

1. A demand valve having a movable diaphragm and valve means operable by movement of the diaphragm from a first position wherein the valve means is closed to a second position wherein the valve means is opened to supply gas to a user, the demand valve comprising:

a housing;

a resilient latching arrangement operable to retain the diaphragm in the first position, wherein the resilient latching arrangement comprises:

a first detent mounted to the diaphragm;

the second detent mounted to the housing and facing in the opposite direction to the first detent; and a resilient swinging arm pivotally mounted to the housing for swinging movement between a latched position and a released position;

and wherein:

in the latched position the resilient swinging arm engages the second detent to retain the resilient swinging arm in the latched position and the resilient swinging arm engages the first detent to retain the diaphragm in the first position wherein the valve means is closed;

in the released position the resilient swinging arm is disengaged from the second detent and the diaphragm is free to move to the second position in which the valve means is opened;

the arrangement being such that the resilient latching arrangement is released when the diaphragm is exposed to a predetermined pressure differential;

the resilient swinging arm comprises two spaced cantilever arms spreadable away from each other against resilient force; and the second detent comprises a pair of divergent inclined surfaces engageable with respective ones of the cantilever arms.

2. A demand valve according to claim 1 wherein the valve means comprises a two-stage valve having a pilot stage and a main valve controlled by the pilot stage, and wherein the pilot stage is controlled by the diaphragm.

3. A demand valve according to claim 1 wherein the resilient latching arrangement comprises a detent mounted to a housing of the valve and a resilient element engageable with the detent and with the diaphragm to retain the diaphragm in the first position.

4. A demand valve according to claim 3 wherein the resilient element comprises an elongate arm pivotally mounted at one end to the housing for swinging movement about a pivot axis, the arm being resiliently deflectable in a direction parallel to the pivot axis during engagement with the second detent.

5. A demand valve according to claim 4 wherein the resilient element comprises a pair of parallel resilient arms mounted to the housing for swinging movement about a pivot axis perpendicular to both arms.

6. A demand valve according to claim 4 wherein a free end of the arm is engageable with the first detent to retain the diaphragm in the first position and wherein the resilient arm is engageable at a position intermediate its length with said second detent.

7. A demand valve according to claim 1 wherein the second detent is a substantially conical surface engageable at diametrically opposed regions by the respective cantilever arms.

8. A demand valve according to claim 1 wherein the second detent further comprises convergent cam surfaces extending from the widest-spaced ends of the inclined surfaces the cam surfaces operable to spread the cantilever arms as the resilient arm is moved to its latched position.

9. A demand valve according to claim 1 further including setting means engageable with the resilient arm to move the resilient arm to its latched position.

10. A demand valve according to claim 9 wherein the setting means comprises a resilient button.

11. A demand valve according to claim 9 wherein the setting means comprises a spring-loaded plunger.

12. A demand valve according to claim 9 wherein the setting means comprises a lever which is manually operable to move the resilient arm to its latched position.

13. A demand valve according to claim 1 wherein the resilient arm is formed from spring wire, and comprises two substantially parallel legs joined by a cross bar.

14. A demand valve according to claim 1 wherein the first detent is formed by the underside of a flange or saddle attached to an outer face of the diaphragm.

15. A demand valve according to claim 1 wherein the second detent is mounted to a post extending from the housing toward the diaphragm.

16. A demand valve according to claim 15 wherein the post is circular in cross-section and the second detent is a conical surface.

17. A demand valve according to claim 15 wherein the post is rectangular or polygonal in cross-section and the second detent comprises a pair of divergent surfaces.

18. A demand valve for supplying breathable gas to a facepiece or helmet of a breathing apparatus, the demand valve comprising: a housing having a supply port and an outlet port; a main valve for supplying pressurized gas from the supply port to the outlet port; a diaphragm movable between a first position wherein the main valve is closed and a second position wherein the main valve is open, the diaphragm being exposed on one face to pressure at the outlet port and on the other face to ambient pressure and to a second resilient biasing means which urges the diaphragm to move toward its second position; resilient latching means operable to retain the diaphragm in its first position against a force of the second resilient biasing means alone and to be releasable by the force of the second resilient biasing means combined with that of a predetermined pressure difference across the diaphragm caused by subambient pressure at the outlet port of the main valve, a pilot chamber associated with the main valve and having a vent opening, the arrangement being such that closure of the vent opening increases pressure in the pilot chamber and closes the main valve, while opening of the vent opening opens the main valve to permit gas to pass from the supply port to the outlet port, a pilot lever movable between a first position in which the vent opening is closed and a second position in which the vent opening is open, the pilot lever being biased towards the second position by a resilient biasing element, the diaphragm engageable with the pilot lever to move the pilot lever to its second position as the diaphragm moves to its second position, the resilient latching means comprising a first detent mounted to the diaphragm, a second detent mounted to the housing and facing in the opposite direction to the first detent, a resilient swinging arm pivotally mounted to the housing for swinging movement between a latched position and a released position, wherein in the latched position the resilient arm engages the second detent to retain the resilient arm in the latched position, the resilient arm engaging the first detent to retain the diaphragm away from the pilot lever, and in the released position the resilient arm being disengaged from the second detent and the diaphragm being free to move to urge the pilot lever toward its second position.

* * * * *